US010350176B2

(12) United States Patent
Grekov et al.

(10) Patent No.: US 10,350,176 B2
(45) Date of Patent: Jul. 16, 2019

(54) PHARMACEUTICAL COMPOSITION CONSISTING OF DIPHENYLENEIODONIUM FOR TREATING DISEASES CAUSED BY THE PARASITES BELONGING TO THE FAMILY TRYPANOSOMATIDAE

(71) Applicant: ÚSTAV MOLEKULÁRNÍ GENETIKY AV ČR, V.V.I., Prague (CZ)

(72) Inventors: Igor Grekov, Břevnov (CZ); António Pombinho, Faro (PT); Matyáš Šíma, Radotín (CZ); Tetyana Kobets, Prague (CZ); Petr Bartůněk, Prague (CZ); Marie Lipoldová, Prague (CZ)

(73) Assignee: Institute of Molecular Genetics, Academy of Sciences of the Czech Republic (CZ)

( * ) Notice: Subject to any disclaimer, the term of this patent is extended or adjusted under 35 U.S.C. 154(b) by 0 days.

(21) Appl. No.: 15/021,211

(22) PCT Filed: Sep. 19, 2014

(86) PCT No.: PCT/CZ2014/000103
§ 371 (c)(1),
(2) Date: Mar. 10, 2016

(87) PCT Pub. No.: WO2015/039638
PCT Pub. Date: Mar. 26, 2015

(65) Prior Publication Data
US 2016/0220508 A1 Aug. 4, 2016

(30) Foreign Application Priority Data
Sep. 20, 2013 (CZ) .................... 2013-729

(51) Int. Cl.
*A61K 31/03* (2006.01)
*A61K 31/33* (2006.01)
*A61P 33/00* (2006.01)
*A61P 33/02* (2006.01)

(52) U.S. Cl.
CPC .............. *A61K 31/03* (2013.01); *A61K 31/33* (2013.01); *A61P 33/00* (2018.01); *A61P 33/02* (2018.01); *Y02A 50/409* (2018.01)

(58) Field of Classification Search
CPC ......... A61K 31/03; A61K 31/33; A61P 33/00; A61P 33/02
USPC .................................................... 514/753
See application file for complete search history.

(56) References Cited

U.S. PATENT DOCUMENTS

| 6,375,944 | B1* | 4/2002 | Trinchieri | A61K 38/208 424/85.2 |
| 2011/0189166 | A1* | 8/2011 | Boucher | A61K 38/06 424/131.1 |
| 2014/0066362 | A1* | 3/2014 | Nudler | A61K 45/06 514/2.3 |

OTHER PUBLICATIONS

Bisti et al., "Is the reactive oxygen species-dependent-NF-kB activation observed in iron-loaded BALB/c mice a key process preventing growth of Leishmania major progeny and tissue-damage?", 2006, Microbes and Infection, 8(6), pp. 1473-1482.*
Jones et al., "Identification of a k-opioid agonist as a potent and selective lead for drug development against human African trypanosomiasis", 2010, Biochemical Pharmacology, 80(10), pp. 1478-1486.*
Charlton et al., "Repurposing as a strategy for the discovery of new anti-leishmanials: the-state-of-the-art", 2018 (first published online Aug. 14, 2017), Parasitology, 145(2), pp. 219-236. (Year: 2018).*
Holzmuller et al., "Trypanosomatid Infections: How Do Parasites and Their Excreted-Secreted Factors Modulate the Inducible Metabolism?", 2018, Frontiers in Immunology, 9(778), pp. 1-14. doi: 10.3389/fimmu.2018.00778 (Year: 2018).*
Alvar J, Vélez ID, Bern C, Herrero M, Desjeux P, Cano J, Jannin J, den Boer M; the WHO Leishmaniasis Control Team. Leishmaniasis worldwide and global estimates of its incidence. PLoS One. 2012;7(5):e35671.
Coura-Vital W, Marques MJ, Veloso VM, Roatt BM, Aguiar-Soares RD, Reis LE, Braga SL, Morais MH, Reis AB, Carneiro M. Prevalence and factors associated with Leishmania infantum infection of dogs from an urban area of Brazil as identified by molecular methods. PLoS Negl Trop Dis. 2011; 5(8):e1291.
Edwards T, Omollo R, Khalil EA, Yifru S, Musa B, Musa A, Wasunna M, Smith PG, Royce C, Ellis S, Balasegaram M, Hailu A. Single-dose liposomal amfotericin B (AmBisome®) for the treatment of visceral leishmaniasis in East Africa: study protocol for a randomized controlled trial. Trials. 2011;12:66.
Grekov I, Svobodová M, Nohýnková E, Lipoldová M. Preparation of highly infective Leishmania promastigotes by cultivation on SNB-9 biphasic medium. J Microbiol Methods. Dec. 2011;87(3):273-7.
Hirumi H, Hirumi K. Continuous cultivation of Trypanosoma brucei blood stream forms in a medium containing a low concentration of serum protein without feeder cell layers. J Parasitol. Dec. 1989;75(6):985-9.
International Search Report and Written Opinion for related International Application No. PCT/CZ2014/000103, dated Jan. 7, 2015 (6 pages).

(Continued)

*Primary Examiner* — My-Chau T. Tran
(74) *Attorney, Agent, or Firm* — Brinks Gilson & Lione; Ryan L. Marshall; Sarah Goodman (57) ABSTRACT

The invention relates to a new use of diphenyleneiodonium (DPI) as an active substance against parasites of the family Trypanosomatidae, in particular against parasites of the genus *Leishmania* and *Trypanosoma*.

15 Claims, 3 Drawing Sheets

(56) References Cited

OTHER PUBLICATIONS

Kobets T, Badalová J, Grekov I, Havelková H, Svobodová M, Lipoldová M. Leishmania parasite detection and quantification using PCR-ELISA. Nat Protoc. Jun. 2010;5(6):1074-80.

Kobets T, Grekov I, Lipoldova M. Leishmaniasis: prevention, parasite detection and treatment. Curr Med Chem. 2012;19(10):1443-74.

Kono H, Rusyn I, Uesugi T, Yamashina S, Connor HD, Dikalova A, Mason RP, Thurman RG. Diphenyleneiodonium sulfate, an NADPH oxidase inhibitor, prevents early alcohol-induced liver injury in the rat. Am J Physiol Gastrointest Liver Physiol. May 2001;280(5):G1005-12.

Kyriakou DS, Alexandrakis MG, Passam FH, Kourelis TV, Foundouli P, Matalliotakis E, Maniatis AN. Quick detection of Leishmania in peripheral blood by flow cytometry. Is prestorage leucodepletion necessary for leishmaniasis prevention in endemic areas? Transfus Med. 2003;13(2):59-62.

Pampiglione S, Manson-Bahr PE, La Placa M, Borgatti MA, Musumeci S. Studies in Mediterranean leishmaniasis. 3. The leishmanin skin test in kala-azar. Trans R Soc Trop Med Hyg. 1975; 69(1):60-8.

Petersen CA. Leishmaniasis, an emerging disease found in companion animals in the United States. Top Companion Anim Med. 2009; 24(4):182-8.

Riera C, Fisa R, López-Chejade P, Serra T, Girona E, Jiménez M, Muncunill J, Sedeño M, Mascaró M, Udina M, Gállego M, Carrió J, Forteza A, Portús M. Asymptomatic infection by Leishmania infantum in blood donors from the Balearic Islands (Spain). Transfusion. Jul. 2008;48(7):1383-9.

Sundar S, Chakravarty J, Agarwal D, Rai M, Murray HW. Single-dose liposomal amphotericin B for visceral leishmaniasis in India. N Engl J Med. 2010;362(6):504-12.

Sundar S, Singh A, Rai M, Prajapati VK, Singh AK, Ostyn B, Boelaert M, Dujardin JC, Chakravarty J. Efficacy of miltefosine in the treatment of visceral leishmaniasis in India after a decade of use. Clin Infect Dis. 2012; 55(4):543-50.

Yuan J, Johnson RL, Huang R, Wichterman J, Jiang H, Hayton K, Fidock DA, Wellems TE, Inglese J, Austin CP, Su XZ. Genetic mapping of targets mediating differential chemical phenotypes in Plasmodium falciparum. Nat Chem Biol. Oct. 2009;5(10):765-71.

* cited by examiner

PHARMACEUTICAL COMPOSITION CONSISTING OF DIPHENYLENEIODONIUM FOR TREATING DISEASES CAUSED BY THE PARASITES BELONGING TO THE FAMILY TRYPANOSOMATIDAE

RELATED APPLICATIONS

The present patent document is a continuation of PCT Application No. PCT/CZ2014/000103, filed Sep. 19, 2014, designating the United States and published in English, which claims the benefit of priority to CZ Patent Application No. 20130000729, filed Sep. 20, 2013, the entire contents of each of which are incorporated herein by reference.

FIELD OF THE INVENTION

The present invention relates to a new use of diphenyleneiodonium (DPI) as active substance against parasites of the family Trypanosomatidae, in particular against parasites of the genus *Leishmania* and *Trypanosoma*.

BACKGROUND OF THE INVENTION

Parasites of the genus *Leishmania* threaten the population of 98 countries on 5 continents [Alvar et al. 2012]. Leishmaniasis, a disease caused by parasitic protozoa *Leishmania* (including, for example. *L. aethiopica, L. donovani, L. infantum, L. major, L. mexicana, L. tropica*), occurs in intertropical zones of America and Africa and extends into the temperate zone of South America, Asia and southern Europe. Depending on body part that is affected by the disease, three types of leishmaniasis are distinguished: cutaneous, muco-cutaneous and visceral. It is assumed that 2 million people (1.5 million of cutaneous leishmaniasis, 0.5 million of visceral leishmaniasis) are newly infected per year and 20,000 to 40,000 people die from the disease per year, whereas recently the total number of affected people reaches 12 million worldwide [WHO, 2012]. Since the reporting of the disease is mandatory only in 32 of the 98 countries affected by leishmaniasis, a large part of the sick people is not recorded anywhere. The disease threatens not only the residents of endemic countries, but also travellers [Kobets et al. 2012] and military forces located in these areas. Effective vaccine against the infection does not exist and the drugs in use have many undesirable side effects. In addition, parasites became resistant against these drugs in many areas [Kobets et al. 2012].

The impact of leishmaniasis on the health of the population was strongly underestimated for many years. In the last 10 years, due to climatic and environmental changes, wars and other unknown effects the endemic areas have been heavily extended and the number of reported cases increased. In Europe, for example, leishmaniasis was previously restricted to the Mediterranean region, but now it has spread to northern Italy and southern Germany, where dozens of cases have been reported in people who did not travel outside said area [Kobets et al. 2012], and recently autochthonous cases of infected animals were reported from Hungary and Switzerland. What is alarming is the fact that *Phlebotomus*, sandfly that transmits *Leishmania*, spreads in a north-eastern direction faster than predicted by the existing models.

Not every person who becomes infected with *Leishmania* will develop a disease. In the Mediterranean region, for example, it is estimated that there is one clinical case for about 30-100 subclinical infections [Pampiglione et al. 1975]. This underreporting can have immense consequences for blood banks. The blood of donors living in endemic areas of Greece were seropositive for *Leishmania* in 15% of cases [Kyriakou et al. 2003], and in the case of donors from endemic regions of Spain (Balearic Islands) in 11% [Riera et al. 2008]. These asymptomatic infections may develop into severe clinical forms in patients with compromised immune system, e. g. AIDS patients. Co-infection with *Leishmania* parasites and HIV is becoming a serious health problem in many countries of the world, because HIV infection increases the risk of developing of visceral leishmaniasis by 100 to 2320 times, and vice versa, *Leishmania* infection increases the risk of onset of AIDS [Kobets et al. 2012].

Dogs infected with *Leishmania* represent a serious problem in veterinary medicine. Infected dogs usually exhibit significant symptoms. However, both diseased and asymptomatic dogs pose a risk to humans because they are a reservoir of parasites, which are transmitted to humans by insects. In some areas of Brazil up to 24% of dogs are infected with *Leishmania* [Coura-Vital et al. 2011], while in some parts of southern Europe, the presence of antibodies against the parasite shows that up to 34% of dogs encountered the infection [Kobets et al. 2012]. In recent years, leishmaniasis was observed in domestic dogs and cats in the USA [Petersen, 2009].

Safe and effective human vaccine against the disease does not exist. Similarly, there is no suitable and simple treatment without side effects [Kobets et al. 2012]. The drugs that are used to treat visceral leishmaniasis [Kobets et al. 2012] and which can be used also for treatment of cutaneous and muco-cutaneous leishmaniasis are: pentavalent antimonials, amphotericin B, liposomal amphotericin B, miltefosine and paromomycin. The oldest chemotherapeutics exploited for the treatment of visceral leishmaniasis are the antimony salts. At present, antimony derivatives sodium stibogluconate (Pentostam) and meglumine antimoniate (Glucantime) are administered as intramuscular or intravenous injection. The disadvantage of these drugs is low clinical efficacy in some areas, the emergence of parasite resistance (up to 60% in the Indian state of Bihar), long duration of treatment (30 days), toxicity and high price. Other chemotherapeutic agents effective in the treatment of leishmaniasis are drugs that were originally developed for the treatment of other diseases. It is a medicine for fighting fungal infections, amphotericin B (AmBisome), a medicine for treating cancer, miltefosine (Impavido), and a broad-spectrum antibiotic, paromomycin. Even these drugs are not ideal. Only miltefosine may be administered per os, but its effectiveness is reduced, and in some cases the administration of miltefosine lead to a patient's death caused by side effects of a drug [Sundar et al. 2012]. Amphotericin B and liposomal amphotericin B require intravenous infusion and paromomycin is administered intramuscularly. Also these drugs have many side effects, they are, except paromomycin, expensive, and just one single mutation is enough to the parasites become resistant to miltefosine. The disadvantage is also the long duration of treatment [Kobets et al. 2012]. Disadvantages of single drugs can be partially reduced by combination therapy [van Griensven et al. 2010]. Successful treatment with a single dose of liposomal amphotericin B in India [Sundar et al. 2010] was described, but these promising results should be still confirmed [Edwards et al. 2011].

The parasitic protozoa of the genus *Trypanosoma* include *T. brucei* and *T. cruzi*, which cause sleeping sickness or Chagas' disease.

Sleeping sickness (also known as African trypanosomiasis) is a human disease caused by the protozoan *Trypanosoma brucei* and transmitted by a tse-tse fly (the flies). The disease is "endemic" in large areas of sub-Saharan Africa (including 36 countries and inhabited by about 60 million people). According to WHO, in 2009 in Africa about 30,000 new cases of the disease were reported. The disease exists in two forms, or is caused by two subspecies: *Trypanosoma brucei gambiense* in West and Central Africa and *Trypanosoma brucei rhodesiense* in eastern and southern Africa, the subspecies listed as the second is much more aggressive and faster-acting. For the treatment of sleeping sickness, depending on the stage of the disease, pentamidine, melarsoprol and suramin are used, however, these drugs exhibit a number of side effects, can cause anaemia or renal damage. Prevention of sleeping sickness is virtually impossible, because there is no effective vaccine.

Chagas disease (also known as American trypanosomiasis) is a tropical parasitic disease caused by the protozoan *Trypanosoma cruzi*, which is transmitted through biting by predatory blood-sucking triatomine bugs (also known as "kissing bugs"). Infected bug transmits the infection only in the case if it discharges infected faeces during the bite. However, the transmission may not occur only through bite of the kissing bugs. The disease can be transmitted by blood from one person to another (for example, during transfusion or organ transplantation, or during pregnancy infected mother can infect her unborn child). WHO estimates that 7-8 million people are infected with this parasite. The incubation period is one to four weeks (in case of infection by blood transfusion, the incubation period may be extended up to 6 weeks). The disease affects mainly the heart, intestine and brain. Medical treatment is effective only in the initial phase of disease and vaccination against disease does not exist. The drugs in use are Nifurtimox and Benznidazol, their disadvantage is considerable toxicity, both drugs cause serious adverse reactions of digestive and nervous system.

*Trypanosoma brucei brucei* causes disease in animals (e.g. horses, camels, water buffalo), but not in humans.

From all the above data it is apparent that there is a need for a new drug with activity against parasitic protozoa of Trypanosomatidae family, which would not require complicated treatment and had fewer side effects than currently used drugs, and would be available in the endemic areas.

Diphenyleneiodonium ([1,1'-biphenyl]-2,2'-diyliodonium, DPI) is a compound having the following formula:

It was shown in rats that diphenyleneiodonium sulphate prevented alcohol-induced liver damage [Kono et al. 2001]. WO 2007/080598 disclosed a pharmaceutical composition comprising DPI or salt thereof for inhibiting neointima proliferation and preventing restenosis. WO 2012/135588 disclosed the use of diphenyleneiodonium chloride as chemotherapeutic agents in the treatment of serous tumours.

The DPI was previously reported that it kills the malaria parasite *Plasmodium falciparum* ($IC_{50}$=0.001-0.00006 µM) [Yuan et al. Nat Chem Biol 5: 765-771, 2009].

The activity of DPI against the parasites of Trypanosomatidae family was not known yet.

DESCRIPTION OF THE INVENTION

The inventors of the present invention tested the library of 2448 chemical compounds including the following collections: "Library of Pharmacologically Active Compounds" (LOPAC1280, Sigma-Aldrich), "Prestwick Chemical Library" (Illkirch, France) and "NIH Clinical Collection" (NIH, USA). The compounds were screened for growth inhibition of the parasite *Leishmania major*. This primary screening resulted in the identification of diphenyleneiodonium (DPI) as an effective inhibitor.

In other tests the inventors surprisingly found that DPI exerts significant activity against parasites of Trypanosomatidae family, *Leishmania major* and *Trypanosoma brucei brucei*. In the tests that were included in the secondary screening, and are described in detail in the Examples, it was shown that DPI effectively inhibits the growth of parasites of the genus *Leishmania* in promastigote form (i.e. form living in the insect vector). The value of $IC_{50}$=0.010 µM was established, which is significantly lower than the value for the current drugs such as amphotericin B ($IC_{50}$=0.039 µM). Moreover, DPI is also effective in killing the parasites of the genus *Leishmania* in amastigote form (i.e. form located in the macrophages), whereas the value of $LD_{50}$=0.066 µM found by the inventors is also lower than the value for the best current drug amphotericin B ($LD_{50}$=0.143 µM).

Furthermore, in vivo tests in infected mice demonstrated that administration of DPI led to a significant reduction in the number of parasites in the spleens of infected mice.

The tests also showed that the blood form of the parasite *Trypanosoma brucei brucei* is killed by treatment with DPI with high efficiency, the value LC50=0.85 µM was observed.

Therefore, DPI may be useful as a medicament for treating diseases caused by parasites belonging to the family Trypanosomatidae, preferably parasites of the genus *Leishmania* and *Trypanosoma*, specifically for example diseases caused by *Leishmania major* or *Trypanosoma brucei brucei*.

One aspect of the present invention relates to diphenyleneiodonium or pharmaceutically acceptable salt thereof for use in treating diseases caused by parasites of the Trypanosomatidae family. Preferably, DPI can be used in treating a disease that is caused by parasites of the genus *Leishmania* and *Trypanosoma*. More preferably, it is used in the treatment of disease caused by the parasite *Leishmania major*. In another more preferred aspect, the application relates to treating a disease caused by the parasite *Trypanosoma brucei brucei*.

Another aspect of the present invention relates to the use of diphenyleneiodonium or pharmaceutically acceptable salt thereof for the manufacturing of a pharmaceutical composition for the treatment of diseases caused by parasites of the Trypanosomatidae family. Preferably, the use relates to the treatment of diseases which are caused by parasites of the genus *Leishmania* and *Trypanosoma*. In one particular embodiment, the use relates to the treatment of disease caused by the parasite *Leishmania major*. In another particular embodiment, the use relates to the treatment of disease caused by the parasite *Trypanosoma brucei brucei*.

A pharmaceutical composition comprising a DPI or a pharmaceutically acceptable salt thereof is useful for treating humans or can be used in veterinary medicine. Medical treatment should be understood as both prophylaxis and curative treatment.

In the pharmaceutical preparation DPI may also be present in the form of pharmaceutically acceptable salts of (non-toxic, physiologically acceptable), of inorganic or organic nature. The person skilled in the art is able to routinely prepare suitable salts.

Pharmaceutical compositions comprising DPI or a pharmaceutically acceptable salt thereof as active ingredient may be formulated, for example, for systemic administration, e.g. enteral, e.g. oral administration, e.g. in the form of tablets or capsules, for rectal administration, e.g. in the form of suppositories, for nasal administration or inhalation, e.g. as spray or drops. The compositions may be preferably formulated for parenteral administration such as injection (i.v., i.m., s.c.), or for administration by means of an infusion or implantable reservoir system. Person skilled in the art would appreciate that this list is not exhaustive, and such a person is aware of other suitable methods.

Typically, the active substance is present in the pharmaceutical composition together with excipients, such as fillers, disintegrators, diluents, solvents, binders, emulsifying agents, buffers, stabilizing agents, preservatives and colouring agents. The excipients and their use are well known to the person skilled in the art.

DPI can be comprised in pharmaceutical compositions in combination with another active substance, e.g. with a compound exhibiting a synergistic effect.

The pharmaceutical compositions according to the invention comprise DPI or pharmaceutically acceptable salt thereof in a pharmaceutically effective amount. The method for determining the pharmaceutically effective amount is a routine procedure well known to the person skilled in the art.

The determination of a dose of DPI in the unit dosage form, e.g. capsule, or suitable concentration in solution, e.g. solution for injection or infusion, is a routine procedure that is known to a person skilled in the art.

The above mentioned expert knowledge concerning the pharmaceutical products, pharmaceutical forms, excipients, etc. are summarized in specialized handbooks (Gennaro, A. R. et al. Remington: The Science and Practice in Pharmacy. 20. Edition. Lippincot Williams & Wilkins, Baltimore, Md., 2000, Kibbe, A. H. Handbook of Pharmaceutical Excipients. Pharmaceutical Press, London, 2000, Chalabala, M. et al.: Technologie léků (Medicaments Technology), Galén, Praha, 2001) readily available to persons skilled in the art, and also in the Czech Pharmacopoeia (ČL 2009), in the European Pharmacopoeia (Ph. Eur.) and/or in the U.S. Pharmacopoeia (USP).

DESCRIPTION OF THE FIGURES

FIG. 1. Effect of DPI on *Leishmania major* in promastigote form (A), including strains resistant to antimony salts (B)

EXAMPLES OF THE INVENTION

Example 1

Primary Screening

DPI was identified when testing the library of 2448 chemical compounds comprising "Library of Pharmacologically Active Compounds" (LOPAC1280, Sigma-Aldrich), "Prestwick Chemical Library" (Illkirch, France) and "NIH Clinical Collection" (NIH, USA). The compounds were reformatted into 384-well polypropylene plates (Corning, cat. No. 3657) at a final concentration of 1 µM in DMSO and used to screen the growth inhibition of the parasite *Leishmania major*.

Primary screening resulted in the finding that DPI is a potent inhibitor of the growth of *Leishmania major*. Therefore DPI, in the form of diphenyleneiodonium chloride, was further tested in in vitro experiments (Sigma, St. Louis, Mo., cat. No. D2926) and in vivo experiments (Sigma, St. Louis, Mo., cat. No. D2926, or AG Scientific, San Diego, Calif., cat. No. D-1011), as will be described in the following examples.

Example 2

Figure 1A:
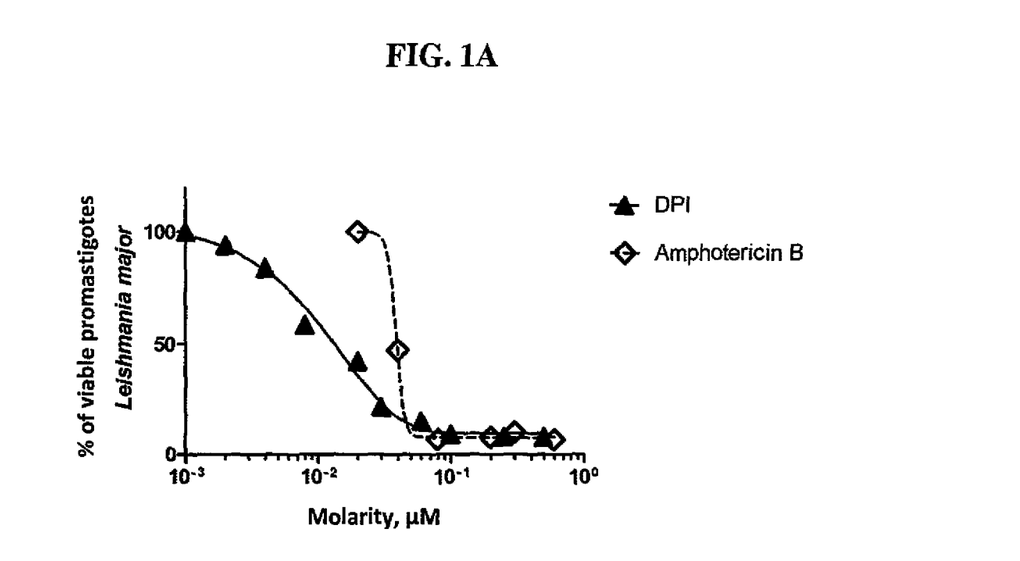
Figure 1B:
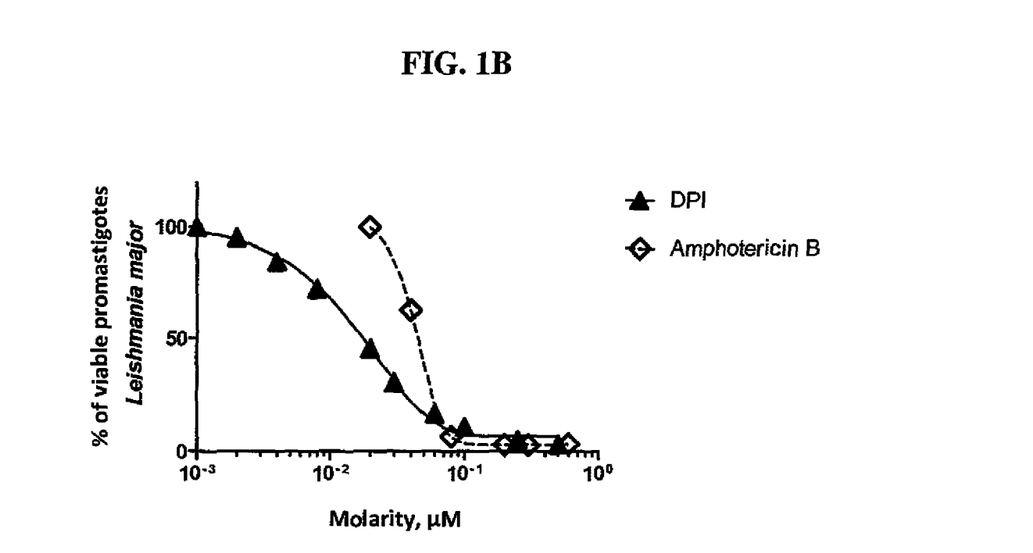

Cytostatic Effect DPI on *Leishmania major* in Promastigote Form (FIG. 1A, 1B)

Antiparasitic activity in culture of promastigotes (insect form) was measured using a standard microdiluting method, determining the minimum inhibitory concentration (MIC) of the test sample, which leads to inhibition of parasite growth.

*Leishmania major* LV 561 (MHOM/IL/67/LRC-L137 JERICHO II) was stored in the overlay of 10% dimethylsulfoxide in liquid nitrogen as subculture 0. Stored samples were thawed and the parasites were cultured for 7 days at 23° C. in a biphasic medium SNB-9 (saline-neopeptone-blood-9) [Grekov et al. 2011]. Solid phase and SNB-9 overlay were prepared from the following ingredients: Bacto™ Agar (Becton, Dickinson and Company, Franklin Lakes, N.J., cat. No. 214010), Bacto™ Neopeptone (Becton, Dickinson and Company, Franklin Lakes, N.J., cat. No. 211681), NaCl and defibrinated rabbit blood (Bioveta, a.s., Ivanovice na Hané, Czech Republic). The overlay solution was supplemented with 50 mg/ml gentamicin (Sigma, St. Louis, Mo., cat. No. G1272). For promastigote growth inhibition assays the subculture 2 of *L. major* was cultured in Schneider's insect medium (Sigma, St. Louis, Mo., cat. No. S0146) supplemented with 50 µm/ml gentamicin (Sigma, St. Louis, Mo., cat. No. G1272), 63.7 µg/ml penicillin G (Sigma, St. Louis, Mo., cat. No. PENK), 100 µg/ml streptomycin (Sigma, St. Louis, Mo., cat. no. S6501), 2% human urine and 10% heat-inactivated fetal bovine serum (Sigma, St. Louis, Mo., cat. No. F2442).

*Leishmania* promastigotes in the logarithmic growth phase were dispensed into black 384-well plates (Corning, New York, N.Y., cat. No. 3571) at a concentration of 15,000 parasites/μl/well using a Multidrop Combi instrument (Thermo Fisher Scientific Inc., Waltham, Mass.). Immediately thereafter DPI (1 nM-500 nM) or amphotericin B (20 nM-10 μM) were added using "pitool" connected to JANUS® Automated Workstation (PerkinElmer Inc., Waltham, Mass.) and incubated for 48 hours. The metabolic capacity of the parasite was measured after 2.5 hours of incubation using the CellTiter-Blue® Reagent (Promega Corporation, Madison, Wis., cat. No. G8082) using EnVision Multilabel Reader (PerkinElmer Inc., Waltham, Mass.). Data were analyzed using non-linear regression (log (inhibitor) vs. response-variable slope). Preparation of the graphs and $IC_{50}$ calculation were performed using GraphPad Prism 5 software (GraphPad Software, USA). The $IC_{50}$ value was calculated by non-linear regression method as the concentration of DPI in which the number of viable promastigotes was reduced by 50% (values given below in Table 1).

Effect of DPI against *Leishmania major* promastigotes, determined as described above, is illustrated in FIGS. 1A and 1B (including strains resistant to antimony salts). The figures show the percentage of living *L. major* promastigotes in cultures to which DPI or amphotericin B were added in comparison with the control culture (taken as 100%).

Figure 2:
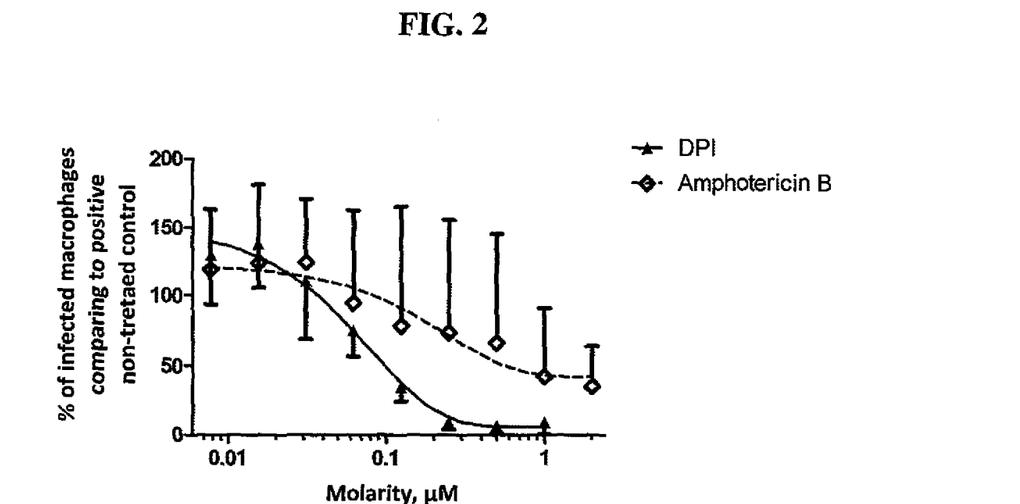
FIG. 2. Effect of DPI on *Leishmania major* in amastigote form (the form that lives in host macrophages)

Cytotoxic Effect of DPI on *Leishmania major* in Amastigote Form (FIG. 2)

Macrophage precursors were isolated from bone marrow and incubated for 7 days at 37° C. and 5% $CO_2$ in DMEM supplemented with supernatant of L929 cells (20 percent by volume) containing M-CSF. After differentiation the macrophages were infected with E-GFP-*L. major* in stationary phase of growth at a ratio of 1:10. Then the macrophages were incubated in DMEM supplemented with the supernatant of L929 cells (20% volume) containing M-CSF at 37° C. and 5% $CO_2$. After 24 hours, the medium containing the extracellular parasites was discarded and the plates were washed 3 times with HBSS medium (Hanks' Balanced Salt Solution, Sigma, St. Louis, Mo., cat. No. H9269). In the final stage HBSS was replaced with supplemented DMEM and the samples were incubated for another 24 hours to be able to transform the promastigotes into amastigotes. Then test substances were added in concentrations of 7.8 nM to 2 nM. After 48 hours of co-incubation with the substances macrophages were stained with 1 µg/ml Laser Dye Styryl-751 (LDP-751) in the dark at room temperature for 30 minutes. Then the medium was aspirated, the macrophages were washed away from the plate with cold PBS containing 10 mM glucose (Sigma, St. Louis, Mo., cat. No. G5400) and 3 mM EDTA (Sigma, St. Louis, Mo., cat. No. ED) and transferred to a round-bottomed plates (Corning, New York, N.Y., cat. No. 3365).

The samples were analyzed on a FACSCalibur flow cytometer (Becton, Dickinson and Company, Franklin Lakes, N.J.) using CellQuest Pro software (Becton, Dickinson and Company, Franklin Lakes, N.J.). Used detectors: Forward Scatter (FSC) (forward scattering), Side Scatter (SSC) (side scattering), FL1 (emission at 530±15 nm) detector for GFP, FL3 (emission>670 nm-"longpass filter") detector for LDS-751. The results were measured for 10,000 macrophages in the first experiment and for 20,000 macrophages in the second experiment. Dead cells negative for LDS-751 were excluded from the analysis. The results were processed using a non-linear regression (log (inhibitor) vs. response-variable slope).

The results of the above assay are shown graphically in FIG. 2.

To check the above results obtained by flow cytometry (FCM) cell smears were prepared from cell suspensions of peritoneal macrophages treated with DPI at concentrations of 2.7 nM, 24.7 nM, 0.222 µM and 2.0 µM. Smears were stained with Giemsa (Sigma, St. Louis, Mo., cat. No. 11700) and analysed by fluorescence microscopy Leica6000DM (Leica Microsystems GmbH, Wetzlar, Germany) at a magnification 400x. The total number of parasites in 500 macrophages was determined. The results were processed using nonlinear regression ("one phase exponential decay").

The $LD_{50}$ values for both flow cytometry and cell smears were calculated as the concentration at which the number of infected macrophages decreased by 50%. Graphs were created and the $LD_{50}$ value calculated using GraphPad Prism 5 software (GraphPad Software, USA). $IC_{50}$ and $LD_{50}$ values are shown in Table 1.

TABLE 1

$LD_{50}$ and $IC_{50}$ values determined from assays results of which are shown in FIG. 1A, 1B and 2 B.

| | DPI | Amph B |
|---|---|---|
| *L. major*, in promastigote form ($IC_{50}$, µM) | 0.010 | 0.039 |
| *L. major*, antimony salts resistant, in promastigote form ($IC_{50}$, µM) | 0.015 | 0.043 |
| *L. major*, in intracellular amastigote form ($LD_{50}$, µM) | 0.066 | 0.143 |

Amph B = amphotericin B

Tests showed that the DPI is effective in inhibiting the growth of parasites of the genus *Leishmania* in promastigote form (a form living in the insect vectors). The value $IC_{50}=0.010$ is significantly lower than the value for current drugs such as amphotericin B ($IC_{50}=0.039$ µM).

Furthermore, it was demonstrated that the DPI is effective in killing the parasites of the genus *Leishmania* in amastigote form (form located in macrophages). The value $LD_{50}=0.066$ µM found for DPI is significantly lower than the value for amphotericin B ($LD_{50}=0.143$ µM).

Example 3

Figure 3:
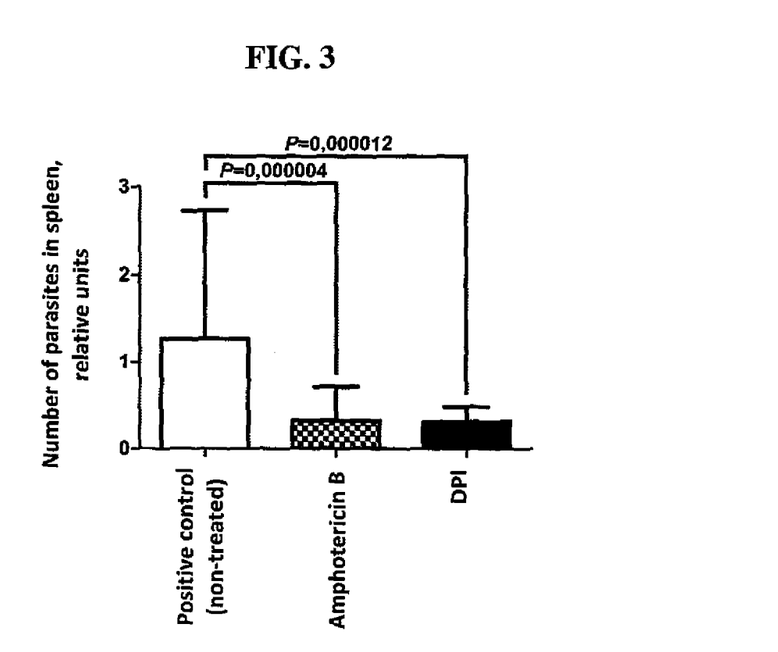
FIG. 3. Effect of DPI in vivo on reduction of the number of parasites in the spleens of infected mice FIG. 4. Effect of DPI on blood form of the parasite *Trypanosoma brucei brucei*

Effect of DPI In Vivo (FIG. 3)

Female BALB/c mice (8-11 weeks old) were randomly divided into four experimental groups of 8-9 animals: 1) non-infected control; 2) the infected untreated control; 3) administration of 2.5 mg/kg/day (MKD) amphotericin B; 4) administration of 0.5 MKD DPI. Promastigotes *L. major* ($10 \times 10^6$) of the 7-day subculture 2 in 50 µl sterile saline (PBS) were subcutaneously inoculated to the root of mouse's tail. Non-infected control mice were inoculated with sterile saline. Application of standard drug (amphotericin B) and test substance (DPI) began the second week after infection when the majority of mice had developed a swelling at the site of parasite injection. During the following 28 days, Group 3 was treated daily by intraperitoneal injection of standard drug amphotericin B, and group 4 by injection of DPI in 20% DMSO in PBS, and groups 1 and 2 by an equal volume of 20% DMSO in PBS. Size of skin lesion was measured weekly using caliper. Mice were sacrificed 6 weeks after infection and the spleen was removed for analysis. Number of parasites in the spleen was determined using the PCR-ELISA according to the procedure described in Kobets et al. Nature Protocols, 5 (6): 1074-1080, 2010. Briefly, total DNA was isolated using standard procedures (http://www.mrcgene.com/tri.htm) TRI reagent (Molecular Research Center, Cincinnati, USA). For PCR amplification, primers were: digoxigenin-labeled F primer 5-ATT TTA CAC CAA CCC CCA GTT-3' and biotinylated R primer 5'-GTG GGG GAG GGG CGT TCT-3' (VBC Genomics Biosciences Research, Austria) targeting 120 bp conserved region of DNA on *Leishmania* kinetoplast minicircle. Each reaction was performed using 50 ng of isolated DNA. 20 ng of *L. major* DNA was used as a positive control and amplificate served as the highest concentration standard. PCR amplification was performed with 30 cycles. A number of parasites was determined by analysis of the PCR product using a modified ELISA protocol (Pharmingen, San Diego, USA). Concentration of *Leishmania* DNA was evaluated using ELISA Reader Tecan and program KIM-E (Schoeller Pharma, Prague, Czech Republic), in which the calibration curve was evaluated by linear least squares regression analysis.

Effect of DPI in vivo on reduction of *L. major* parasites in the spleen of infected mice is shown in FIG. 3.

In the above described in vivo assay it was demonstrated that administration of DPI resulted in statistically significant reduction in the number of parasites in the spleen of infected mice, at a comparable level to that observed for a group treated with standard drug amphotericin B.

Example 4

Figure 4:
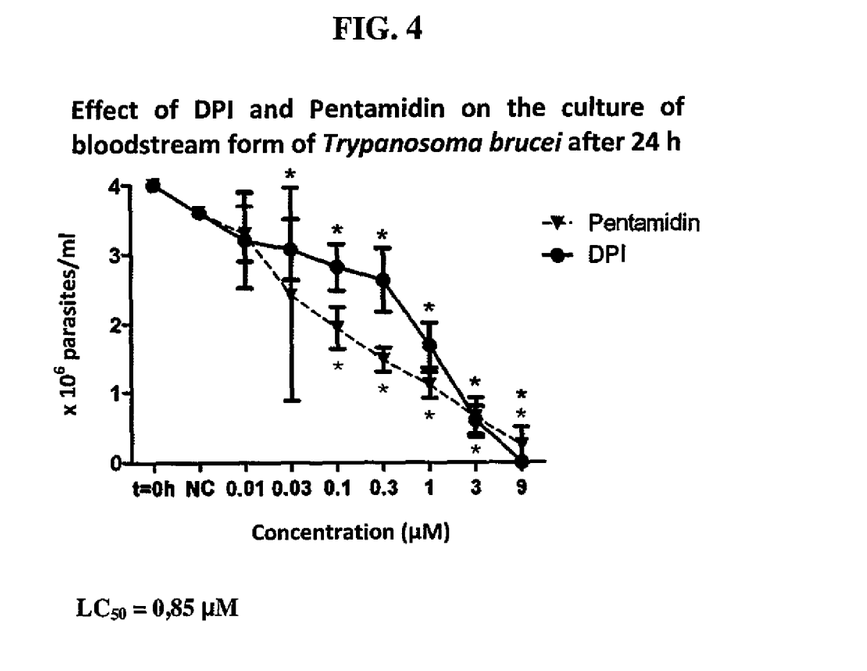

Effect of DPI on Bloodstream Form of the Parasite *Trypanosoma brucei brucei* (FIG. 4)

*Trypanosoma brucei brucei* AnTar1 was a gift from Jan van den Abbeele, Institute of Tropical Medicine "Prince Leopold", Antwerp, Belgium. Parasites were stored in liquid nitrogen and before the experiment they were thawed and used to infect mice by intraperitoneal inoculation. Six to seven days after infection, the infected mice were sacrificed by cervical dislocation, the blood was taken from the chest cavity after disruption of the aorta and mixed in a ratio of 1:5 with HMI-11 (Iscove's modified medium (Sigma, St. Louis, Mo., cat. No. I6529) supplemented with 1.5 mM L-cysteine, 0.2 mM 2-mercaptoethanol, 1 mM sodiumpyruvate, 0.16 mM thymidine, 100 µg/ml streptomycin, 63.7 µg/ml penicillin G and 20% heat-inactivated FBS) [Hiru Hiru & 1989]. The suspension was centrifuged at 200 g for 5 minutes at 4° C. and the supernatant was collected. Number of bloodstream forms of *T. brucei brucei* in the supernatant was determined by counting in a Barker chamber. The culture was then diluted in HMI-11 to a density of $4\times10^6$ parasites/ml, and the parasites were cultured for 3 hours at 37° C., 5% $CO_2$ in 48-well culture plates (Costar, cat. No. 3548), 0.5 ml/well. Plates were then covered with parafilm to prevent gas exchange, and cultured overnight at 37° C. The parasites survived another 24 hours at approximately the same density and then they could be used to test the antiparasitic effects of DPI.

To determine the antiparasitic effects of DPI the parasites were cultured according to the procedure described above. At the beginning of cultivation DPI was added to the test cultures resulting in different molar concentrations (0.01, 0.03, 0.1, 0.3, 1, 3 and 9 µM). Parallel cultures were tested with the same concentrations of pentamidine (potassium salt of pentamidine), which served as the reference substance (it is a drug that is commonly used), and the cultures without addition of active substances as a control. Two independent experiments were carried out, and in each of them individual cultures were conducted in duplicate. Numbers of live parasites (moving cells) in individual cultures were counted after 24 h of cultivation in Barker chamber.

Effect of DPI on bloodstream form of the parasite *Trypanosoma brucei brucei* is illustrated graphically in FIG. 4. For DPI, value of $LC_{50}=0.85$ µM was observed, which is higher than a value for the reference substance pentamidine ($LC_{50}=0.14$ µM). However, it is interesting that DPI acts both on *Leishmania* and on *Trypanosoma*. This indicates the fact that the DPI can act on a common mechanism of these parasites. $LC_{50}$ value was designated as the concentration which causes a reduction of live parasites by 50% compared to the negative control. $LC_{50}$ values were determined using the three parameter curve log (inhibitor) vs. response in GraphPad Prism 5 (GraphPad Software, USA). This curve has been selected as suitable for fitting of the measured data. The curve was fitted to the data by least squares analysis.

Example 5

Figure 5:
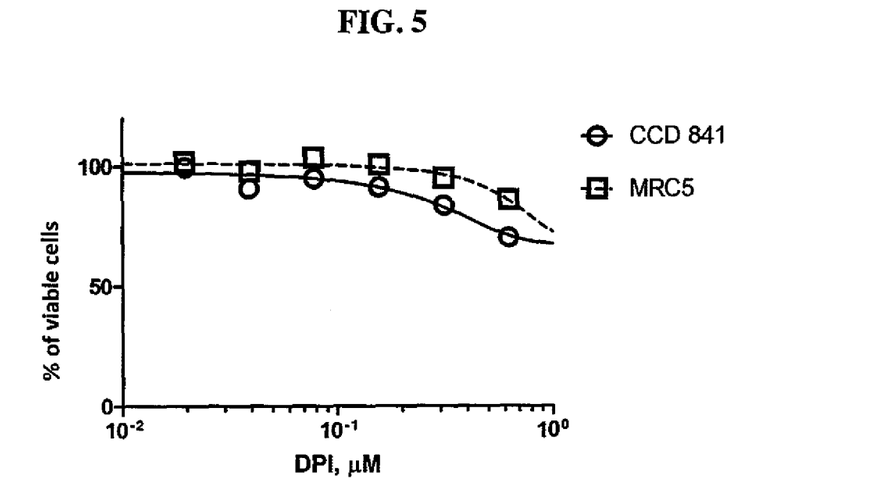
FIG. 5. Determination of DPI effect on the viability of human cells

Determination of Cytotoxicity of DPI for Human Cells (FIG. 5)

Human cells CCD 841 (intestinal epithelial cells) and MRC5 (fetal lung fibroblasts) in appropriate growth media were dispensed into black 384-well plates (Corning, cat. No. 3571) at a density of 15,000 cells/25 µl/well using a Multidrop Combi (Thermo Scientific). After 48 hours incubation at 37° C. and 5% $CO_2$, cell viability was determined using a commercial assay CellTiter Blue Cell Viability Assay (Promega, cat. No. G8082). Cytotoxicity was determined after 4 hours at 37° C. and 5% $CO_2$ using a commercial assay CytoTox-ONE Homogenous Membrane Integrity Assay (Promega, cat. No. G7892). Fluorescence intensity was measured by the detector (reader) EnVision (Perkin Elmer), and measured data were analysed using the software Prism5 (GraphPad Software, Inc.).

Viability of cells as depending on concentration of DPI is shown in FIG. 5. Concentrations of DPI, where significant anti-parasitic activity occurs, i.e. in the range of 9.8 nM-1.25 µM (see examples 1 and 2), showed no negative effect on the viability of human CCD 841 and MRC5 cells. Hence, anti-parasitically effective concentrations of DPI are not cytotoxic to human cells.

REFERENCES

Alvar J, Vélez I D, Bern C, Herrero M, Desjeux P, Cano J, Jannin J, den Boer M; the WHO Leishmaniasis Control Team. Leishmaniasis worldwide and global estimates of its incidence. PLoS One. 2012; 7(5):e35671.

Coura-Vital W, Marques M J, Veloso V M, Roatt B M, Aguiar-Soares R D, Reis L E, Braga S L, Morais M H, Reis A B, Carneiro M. Prevalence and factors associated with *Leishmania infantum* infection of dogs from an urban area of Brazil as identified by molecular methods. PLoS Negl Trop Dis. 2011; 5(8):e1291.

Edwards T, Omollo R, Khalil E A, Yifru S, Musa B, Musa A, Wasunna M, Smith P G, Royce C, Ellis S, Balasegaram M, Hailu A. Single-dose liposomal amfotericin B (AmBisome®) for the treatment of visceral leishmaniasis in East Africa: study protocol for a randomized controlled trial. Trials. 2011; 12:66.

Grekov I, Svobodová M, Nohýnková E, Lipoldová M. Preparation of highly infective *Leishmania* promastigotes by cultivation on SNB-9 biphasic medium. J Microbiol Methods. 2011 December; 87(3):273-7.

Hirumi H, Hirumi K. Continuous cultivation of *Trypanosoma brucei* blood stream forms in a medium containing a low concentration of serum protein without feeder cell layers. J Parasitol. 1989 December; 75(6):985-9.

Kobets T, Badalová J, Grekov I, Havelková H, Svobodová M, Lipoldová M. *Leishmania* parasite detection and quantification using PCR-ELISA. Nat Protoc. 2010 June; 5(6):1074-80.

Kobets T, Grekov I, Lipoldova M. Leishmaniasis: prevention, parasite detection and treatment. Curr Med Chem. 2012; 19(10):1443-74.

Kona H, Rusyn I, Uesugi T, Yamashina S, Connor H D, Dikalova A, Mason R P, Thurman R G. Diphenyleneiodonium sulfate, an NADPH oxidase inhibitor, prevents early alcohol-induced liver injury in the rat. Am J Physiol Gastrointest Liver Physiol. 2001 May; 280(5):G1005-12.

Kyriakou D S, Alexandrakis M G, Passam F H, Kourelis T V, Foundouli P, Matalliotakis E, Maniatis A N. Quick detection of *Leishmania* in peripheral blood by flow cytometry. Is prestorage leucodepletion necessary for leishmaniasis prevention in endemic areas? Transfus Med. 2003; 13(2):59-62.

Pampiglione S, Manson-Bahr P E, La Placa M, Borgatti M A, Musumeci S. Studies in Mediterranean leishmaniasis. 3. The leishmanin skin test in kala-azar. Trans R Soc Trop Med Hyg. 1975; 69(1):60-8.

Petersen C A. Leishmaniasis, an emerging disease found in companion animals in the United States. Top Companion Anim Med. 2009; 24(4):182-8.

Riera C, Fisa R, López-Chejade P, Serra T, Girona E, Jiménez M, Muncunill J, Sedeño M, Mascaró M, Udina M, Gállego M, Carrió J, Forteza A, Portús M. Asymptomatic infection by *Leishmania infantum* in blood donors from the Balearic Islands (Spain). Transfusion. 2008 July; 48(7): 1383-9.

Sundar S, Chakravarty J, Agarwal D, Rai M, Murray H W. Single-dose liposomal amphotericin B for visceral leishmaniasis in India. N Engl J Med. 2010; 362(6):504-12.

Sundar S, Singh A, Rai M, Prajapati V K, Singh A K, Ostyn B, Boelaert M, Dujardin J C, Chakravarty J. Efficacy of miltefosine in the treatment of visceral leishmaniasis in India after a decade of use. Clin Infect Dis. 2012; 55(4): 543-50.

WHO: Leishmaniasis (http://www.who.int/leishmaniasis/en/) (Jan. 8, 2012)

Yuan J, Johnson R L, Huang R, Wichterman J, Jiang H, Hayton K, Fidock D A, Wellems T E, Inglese J, Austin C P, Su X Z. Genetic mapping of targets mediating differential chemical phenotypes in *Plasmodium falciparum*. Nat Chem Biol. 2009 October; 5(10):765-71.

The invention claimed is:

1. A method of inhibiting growth of or killing a parasite, comprising administering diphenyleneiodonium or a pharmaceutically acceptable salt thereof to a parasite-infected mammal without coadministering another active substance, wherein the parasite is in the parasitic family Trypanosomatidae.

2. The method according to claim 1, wherein the parasite belongs to the genus *Leishmania*.

3. The method according to claim 2, wherein the parasite is *Leishmania major*.

4. The method according to claim 1, wherein the parasite belongs to the genus *Trypanosoma*.

5. The method according to claim 4, wherein the parasite is *Trypanosoma brucei brucei*.

6. A method of inhibiting growth of or killing a parasite, the method consisting of administering diphenyleneiodonium or a pharmaceutically acceptable salt thereof along with a pharmaceutically acceptable carrier and/or excipient to a parasite-infected mammal, wherein the parasite is in the parasitic family Trypanosomatidae.

7. The method according to claim 6, wherein the parasite belongs to the genus *Leishmania*.

8. The method according to claim 7, wherein the parasite is *Leishmania major*.

9. The method according to claim 6, wherein the parasite belongs to the genus *Trypanosoma*.

10. The method according to claim 9, wherein the parasite is *Trypanosoma brucei brucei*.

11. A method of inhibiting growth of or killing a parasite, consisting of administering a pharmaceutical composition consisting of an anti-parasitically effective dose of diphenyleneiodonium or a pharmaceutically acceptable salt thereof along with a pharmaceutically acceptable excipient to a parasite-infected mammal, wherein the parasite is in the parasitic family Trypanosomatidae.

12. The method according to claim 11, wherein the parasite belongs to the genus *Leishmania*.

13. The method according to claim 11, wherein the parasite is *Leishmania major*.

14. The method according to claim 11, wherein the parasite belongs to the genus *Trypanosoma*.

15. The method according to claim 14, wherein the parasite is *Trypanosoma brucei brucei*.

* * * * *